United States Patent
Fervel et al.

(10) Patent No.: US 9,726,600 B2
(45) Date of Patent: Aug. 8, 2017

(54) DEVICE FOR THE REMOTE OPTICAL DETECTION OF GAS

(71) Applicant: Bertin Technologies, Montigny le Bretonneux (FR)

(72) Inventors: Franck Fervel, Peynier (FR); Philippe Bernascolle, Tourves (FR)

(73) Assignee: BERTIN TECHNOLOGIES, Montigny le Bretonneux (FR)

( * ) Notice: Subject to any disclaimer, the term of this patent is extended or adjusted under 35 U.S.C. 154(b) by 0 days.

(21) Appl. No.: 14/646,531

(22) PCT Filed: Nov. 20, 2013

(86) PCT No.: PCT/FR2013/052807
§ 371 (c)(1),
(2) Date: May 21, 2015

(87) PCT Pub. No.: WO2014/080127
PCT Pub. Date: May 30, 2014

(65) Prior Publication Data
US 2015/0300949 A1    Oct. 22, 2015

(30) Foreign Application Priority Data
Nov. 22, 2012 (FR) ...................... 12 61138

(51) Int. Cl.
*G01N 21/3504* (2014.01)
*G01N 33/00* (2006.01)
(Continued)

(52) U.S. Cl.
CPC ............ *G01N 21/3504* (2013.01); *G01J 3/42* (2013.01); *G01N 21/47* (2013.01);
(Continued)

(58) Field of Classification Search
CPC ................................................. G01N 21/3504
See application file for complete search history.

(56) References Cited

U.S. PATENT DOCUMENTS 4,795,253 A * 1/1989 Sandridge et al. ............. 356/51
6,853,452 B1 * 2/2005 Laufer ............... G01N 21/3504
356/436
(Continued)

FOREIGN PATENT DOCUMENTS

| EP | 0 287 929 | 4/1988 | ............. G01N 21/35 |
| EP | 0 544 962 | 6/1993 | ............. G01N 21/35 |

(Continued)

OTHER PUBLICATIONS

International Search Report from corresponding International Patent Application No. PCT/FR2013/052807, dated Feb. 20, 2014.
(Continued)

*Primary Examiner* — David Porta
*Assistant Examiner* — Hugh H Maupin
(74) *Attorney, Agent, or Firm* — Kusner & Jaffe

(57) ABSTRACT

A detector device for optically detecting a gas in a zone of space under observation, the device comprising a camera and means for continuously detecting at least one gas in the observed zone by analyzing absorbance in a plurality of different spectral bands. The device further comprises a matrix of micromirrors that are individually steerable between at least two positions, in a first of which they reflect the radiant flux coming from the observed zone to the camera for detecting gas in said spectral bands, and in a second of which they reflect the radiant flux coming from the observed zone to a Fourier transform infrared spectroscope.

12 Claims, 2 Drawing Sheets

(51) Int. Cl.
*G01N 21/47* (2006.01)
*G01J 3/42* (2006.01)
*G02B 26/08* (2006.01)

(52) U.S. Cl.
CPC ..... *G01N 33/0031* (2013.01); *G01N 33/0036* (2013.01); *G02B 26/0833* (2013.01)

(56) References Cited

U.S. PATENT DOCUMENTS

2004/0211900 A1* 10/2004 Johnson ................. 250/338.5
2006/0132780 A1* 6/2006 Holland ................. G01J 3/02
356/419
2007/0229821 A1* 10/2007 Christian et al. ............. 356/328

FOREIGN PATENT DOCUMENTS

GB      2 320 155      6/1998    ............. H04N 5/335
WO      WO 03/044499   5/2003    ............. G01N 21/35

OTHER PUBLICATIONS

Robberto, M. et al., "Applications of DMDs for Astrophysical Research," Optomechatronic Micro/Nano Devices and Components III: Oct. 8-10, 2007, Lausanne, Switzerland [Proceedings of SPIE, ISSN 0277-786X], Sipie, Bellingham, Wash., vol. 7210, Jan. 1, 2009, pp. 72100A-1, XP007922732, DOI: 10.1117/12.809542, ISBN: 978-1-62841-730-2.

* cited by examiner

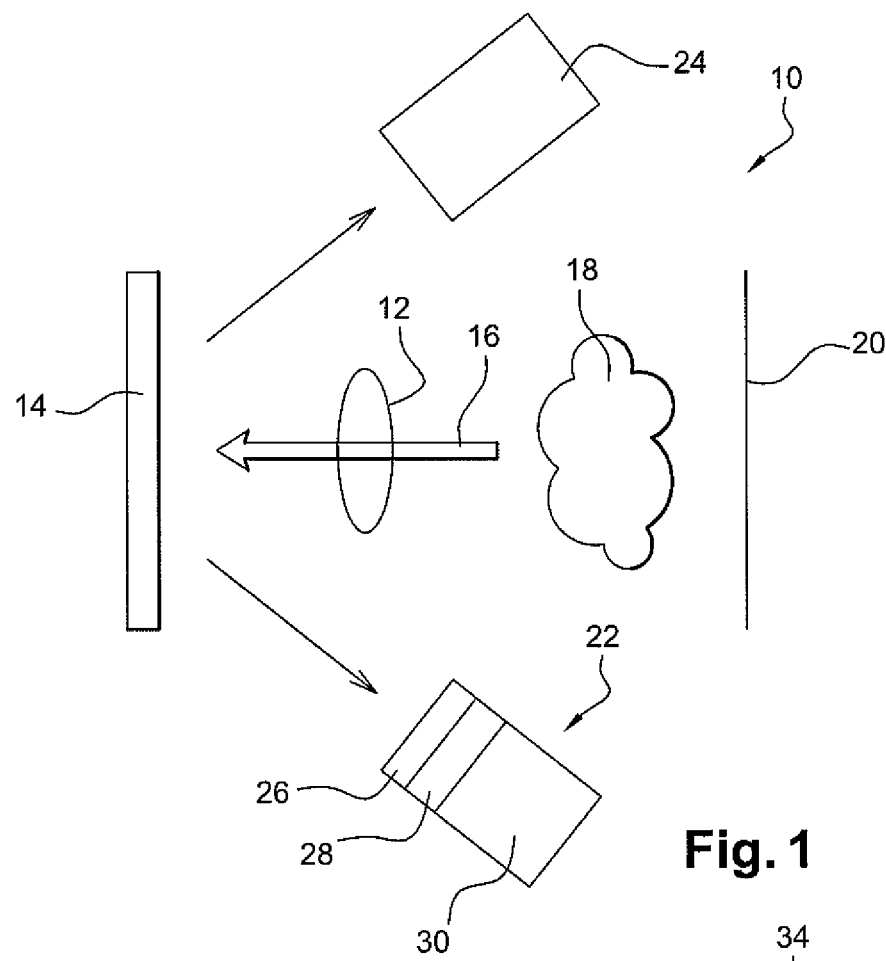
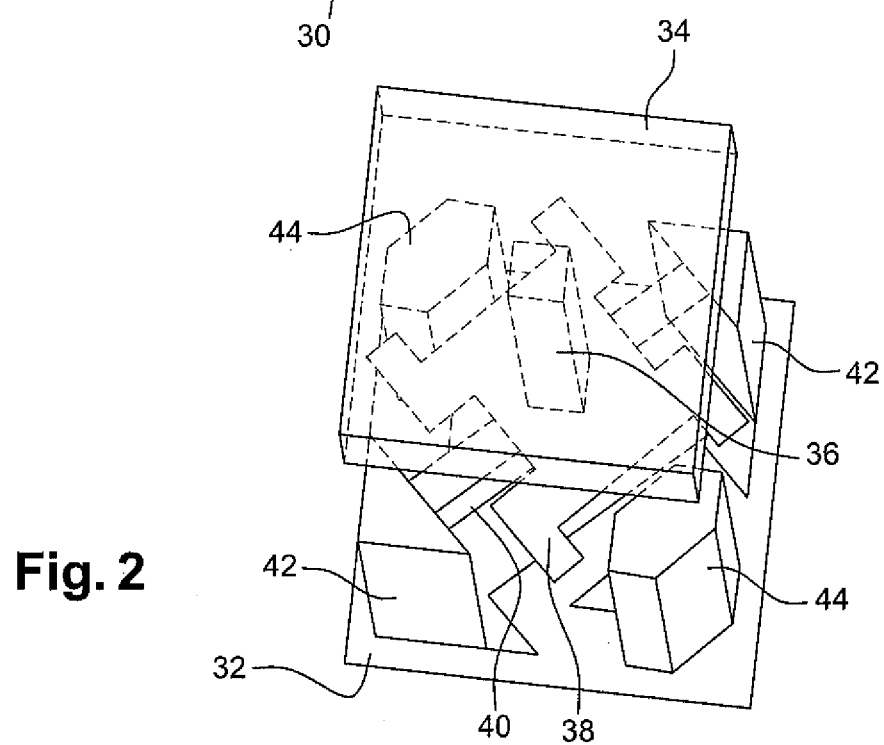

DEVICE FOR THE REMOTE OPTICAL DETECTION OF GAS

FIELD OF THE INVENTION

The invention relates to a device for remote optical detection of a gas, which device is suitable for use in particular for monitoring industrial sites such as chemical factories, refineries, gas storage installations, etc.

BACKGROUND OF THE INVENTION

Documents EP-A-0544962 and WO 03/044499 disclose an infrared imager associated with optical measurement and reference filters that are placed in succession on the optical axis of the imager and that have passbands containing an absorption line of a looked-for gas (for the measurement filters) or that are complementary to said absorption line (for the reference filters). The background of the zone under observation is used as a source of infrared and the presence of a looked-for gas is revealed by differential processing of the infrared images taken through the filters, with the processing making it possible to calculate the concentration of the detected gas.

In practical manner, a set of measurement and reference filters is carried by a motor-driven rotary disk so as to bring the filters in succession onto the optical axis of the imager. The images of the observed zone in the various spectral bands corresponding to the passbands of the filters are acquired sequentially.

That type of device thus enables a given gas to be looked for and analyzed in a zone of space towards which the imager is pointed. Such a device requires prior calibration using a background that emits standard radiant flux when no gas is present. Nevertheless, that type of calibration is found to be relatively inaccurate because of the difficulty of defining a standard background, which background will always be different from the real background, thereby greatly limiting the accuracy of gas concentration measurements. Thus, in practice, that type of device serves essentially for identifying the presence of a given gas, but does not make it possible to indicate accurately its concentration in the zone of space under observation. Furthermore, identifying a given gas requires a measurement filter with a corresponding absorption line to be available, which implies that analyzing a mixture of gases, having a plurality of different absorption lines, is difficult to achieve. The analysis of absorption lines of different chemicals in the zone under observation is limited by the number of filters used. Different chemicals may present absorption lines that are similar.

SUMMARY OF THE INVENTION

A particular object of the invention is to avoid those drawbacks in a manner that is simple, effective, and inexpensive.

To this end, the invention proposes a detector device for optically detecting a gas, e.g. a pollutant, in a zone of space under observation, the device comprising a camera and means for continuously detecting at least one gas in part or all of the observed zone by analyzing absorbance in a plurality of different spectral bands, the device being characterized in that it includes a matrix of micromirrors that are individually steerable between at least two positions, in a first of which they reflect the radiant flux coming from the observed zone to the camera for detecting gas in said spectral bands, and in a second of which they reflect the radiant flux coming from the observed zone to a Fourier transform infrared spectroscope.

The invention combines in a single device means for detection by analyzing absorbance in a plurality of spectral bands and a Fourier transform infrared spectroscope. The coupling between the subassemblies of the device is achieved by means of the micromirror matrix that enables the radiant flux from the observed zone to be reflected to the camera or to the Fourier transform spectroscope.

The use of a spectral band camera enables one or more gases to be detected quickly on a continuous basis in a wide field of view, while a fast Fourier transform infrared spectroscope enables the gas(es) present in the radiant flux from a small zone of the observed scene to be subjected to accurate spectral analysis in order to invalidate or confirm the detection of gas by the camera.

According to another characteristic of the invention, the gas detection means include at least six different spectral bands for detecting gas in said spectral bands.

The micromirror matrix comprises a substrate on which each micromirror is hinged to pivot between its first and second positions by using means for applying an electrostatic field between the substrate and the micromirror.

Preferably, each of the micromirrors is steerable about a pivot so as to cover an angular extent of about 24°.

The invention also provides a method of using a detector device as described above, the method comprising:

a) causing the micromirrors of the matrix to be steered simultaneously so that all of the radiant flux coming from the zone of space under observation is directed to the camera;

b) deducing the presence of a gas, if any, in all or part of the zone of space under observation on the basis of an analysis of the plurality of spectral bands;

c) in the event of the presence of a gas being detected in at least a portion of the observed zone, steering at least some of the micromirrors corresponding to said portion of the observed zone into their second position so as to direct a fraction of the radiant flux coming from said portion to the Fourier transform infrared spectroscope; and d) confirming or invalidating the presence of the detected gas on the basis of a Fourier transform analysis.

The camera collects the radiant flux coming from the observed zone and performs analysis by absorbance in a plurality of spectral bands in the various directions lying within the observed scene.

In the event of a gas being positively identified in a portion of the observed scene, the mirrors of the micromirror matrix corresponding to said portion of space are steered so as to direct the radiant flux from that portion in space to the fast Fourier transform infrared spectroscope in order to perform accurate spectral analysis of the flux and invalidate or confirm the presence of the gas in said portion of space.

BRIEF DESCRIPTION OF THE DRAWINGS

Other advantages and characteristics of the invention appear on reading the following description made by way of non-limiting example and with reference to the accompanying drawings, in which:

FIG. 1 is a diagrammatic view of the device of the invention;

FIG. 2 is a diagrammatic view in perspective of a micromirror in a matrix of micromirrors used in the invention;

DETAILED DESCRIPTION OF THE INVENTION

Figure 3:
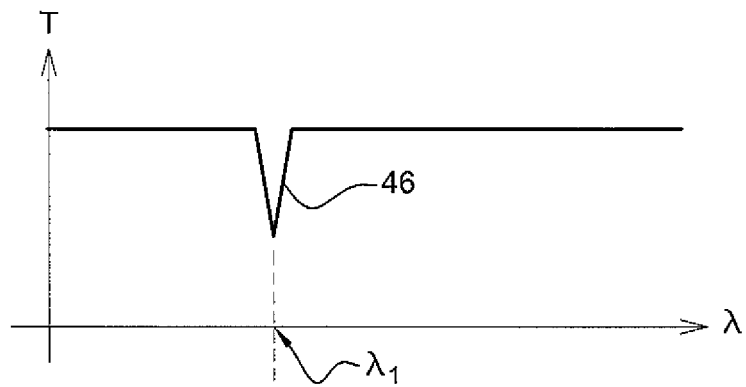
FIG. 3 is highly diagrammatic and shows the appearance of an absorption line of a gas.

Reference is made initially to FIG. 1, which is a diagram showing a detector device 10 of the invention comprising optical means 12 reflecting radiant flux 16 from a zone of space under observation onto a matrix 14 of micromirrors, which zone of space may include for example a cloud of a looked-for gas 18 together with a background 20. The device also has an infrared camera or imager 22 for analyzing absorbance in a plurality of different spectral bands of the radiant flux reflected by the matrix 14 of micromirrors, and a fast Fourier transform infrared spectroscope 24.

The camera essentially comprises an optical system 26 for taking images, filters 28, and at least one sensitive element 30 onto which the optical system forms the image reflected by the matrix 14 of micromirrors.

The micromirror matrix 14 has a plurality of micromirrors carried on a common substrate 32 and individually steerable between a first position in which each of them reflects the radiant flux coming from the absorbed zone towards the camera 22, and a second position in which each of them reflects the radiant flux towards the Fourier transform infrared spectroscope 24 (FIG. 2).

FIG. 2 shows the connection been a micromirror 34 and the substrate 32. Each micromirror is connected by a post 36 to a plate 38 that is itself mounted on a pivot 40 hinged at both ends to turn relative to two arms 42 of the substrate 32. The device has electrodes 44 for applying an electrostatic field between the substrate and the micromirror so as to cause the micromirror 34 to pivot between its first and second positions. Each pivot 40 may include a torsion spring (not shown) mounted about the pivot 40 and secured at its ends to the arms 42 of the substrate 32. The torsion spring of each micromirror is configured so that each micromirror is held in its first position by the torsion force in the absence of an applied electrostatic field.

Thus, when no electrostatic field is applied, the micromirrors reflect the radiant flux towards the camera 22. When an electrostatic force is applied to a micromirror, it pivots so as to tilt into its second position in which it reflects the radiant flux towards the Fourier transform spectroscope 24.

The micromirrors 34 are thus individually steerable about their respective pivots 40, e.g. so as to be capable of covering an angular extent lying in the range −12° to +12° approximately relative to a plane perpendicular to the substrate 32.

Micromirror matrices of this type are sold by numerous suppliers, and in particular by Texas Instruments.

In a particular embodiment, the camera includes at least two filters 28 that are interposed sequentially and in turn, or else in superposition, on the optical axis of the camera 22 by using a motor system.

These two filters 28 have wavelength transmission bands that overlap to a large extent and that are preferably generally similar, except that one of them includes an absorption line of the gas that is to be detected while the other one is substantially complementary to that absorption line. This concept is explained in greater detail with reference to FIGS. 3 to 5.

FIG. 3 is a diagram showing variation in the transmission T of the gas that is to be detected over a certain band of wavelengths $\lambda$, the transmission curve showing an absorption line 46 at a wavelength $\lambda_1$, the amplitude of this absorption line being a function of the concentration of the gas, and its width being of the order of a few tens or a few hundreds of nanometers, for example.

Figure 4:
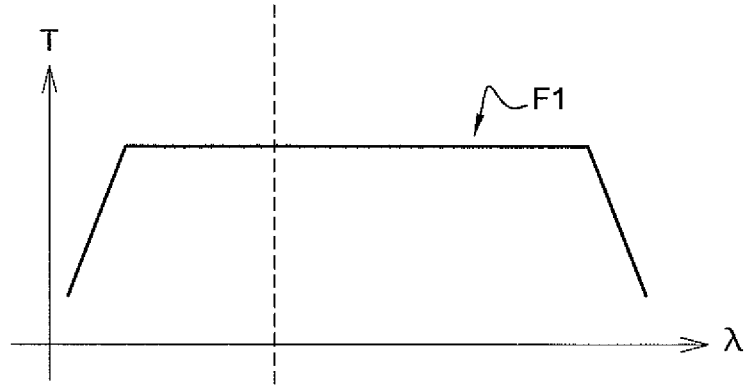
FIGS. 4 and 5 are diagrams showing the transmission bands of two filters, as a function of wavelength.

FIG. 4 is a diagrammatic representation of the transmission curve as a function of wavelength for one of the two filters, e.g. a first filter that is given reference F1. This transmission band includes the wavelength $\lambda_1$ of the absorption line of the gas that is to be detected, and it extends over a wavelength band that is greater than the width of the absorption line 46 of the gas that is to be detected.

Figure 5:
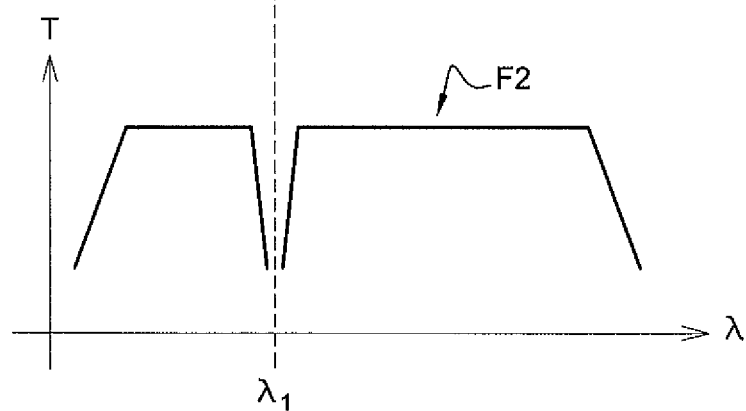

The other filter, given reference F2, has a transmission band of appearance as shown in FIG. 5, that does not include the wavelength $\lambda_1$ of the absorption line 46 of the gas that is to be detected and that is, so to speak, complementary to said absorption line relative to the transmission band of the filter F1 as shown in FIG. 4.

Thus, when the filter F1 is placed on the optical axis of the camera or imager 22, the radiant flux received by the sensitive element is a function of the presence or absence of a cloud 18 of gas that is to be detected in the zone under observation, and is also a function of the concentration of the gas.

When the filter F2 is placed on the optical axis of the camera or the thermal imager 22, the flux that it transmits to the sensitive element is independent of the presence or absence of a cloud 18 of the gas that is to be detected in the observed zone.

The ratio of the fluxes supplied sequentially to the sensitive element through the filter F1 and then through the filter F2 provides a magnitude that is a function of the concentration of the gas that is to be detected in the zone under observation, but that is independent of the temperature and of the transmission path of the radiant flux, i.e. the optical means 12, the micromirror matrix 14, and the image-forming optical means 26 of the camera 22.

In a variant, the filter F1 may be placed on the optical axis, with measurements being taken, and then the filter F2 may be placed on the optical axis while leaving the filter F1 in place, and measurements are taken again.

With the help of several sets of filters having different absorption lines as described above, it is possible to detect on a continuous basis the presence of a plurality of gases in the zone of space under observation.

According to the invention, the micromirror matrix 14 is associated with an infrared spectroscope 24 that serves to obtain an interferogram having all of the frequency components of the zone under observation. A fast Fourier transform makes it possible to view peaks at different wavelengths corresponding to different chemical compounds and to deduce therefrom accurately the presence of chemical compounds in the under observation with spectral resolution that is better than that obtained with the spectral band camera 22. The height of each peak gives accurate information about the concentration of the chemical compound relating to that peak.

According to the invention, the device is used by controlling the micromirrors of the matrix 14 to be steered simultaneously so that all of the radiant flux 16 coming from the zone of space 20 under observation is directed to the camera. Thereafter, absorbance analysis is performed in a plurality of spectral bands as described above in order to deduce whether or not a predetermined gaseous compound corresponding to an absorption line is present. In the event of a gas being detected in a portion of the observed zone, some of the micromirrors in the matrix 14 corresponding to this portion are selected and they are steered simultaneously into their second position so as to direct at least a fraction of the radiant flux coming from that portion to the Fourier transform infrared spectroscope in order to enable it to confirm or invalidate the presence of the detected gas on the basis of Fourier transform analysis. When some of the micromirrors are positioned in their second position, the other micromirrors continue to send the radiant flux to the camera 22, thus making it possible to track in real time the zone of space under observation. The device of the invention may be very compact and can be implemented in the form of a mobile or transportable appliance, thereby making on-site detection and monitoring easier.

In a practical embodiment of the invention, the camera has six to nine filters and the sensitive element 30 of the camera is a sensor having 640 by 480 pixels making it possible, in combination with the optical system 26 to collect radiant flux coming from a zone of space occupying about 30° in the alignment direction of the 640 pixels of the camera and about 24° in the alignment direction of the 480 pixels of the camera.

The Fourier transform spectroscope is capable of analyzing a zone of space that corresponds to a solid angle of 0.5° in one direction by 0.5° in a perpendicular direction. Thus, in practice, only a few micromirrors are steered from their first position to their second position in the event of a gas being successfully detected by the camera 22. In a particular embodiment of the invention, the camera has the same number of pixels as there are micromirrors, The device of the invention combines a camera having a large angular aperture for detecting gas in real time but not suitable for calculating accurately the concentrations of the detected gases, with a Fourier transform spectroscope of small angular aperture but that is capable of detecting accurately the components and their respective concentrations in a given direction in the zone of space under analysis.

Having described the invention, the following is claimed:

1. A detector device for optically detecting a gas in an observed zone of space, the detector device comprising:
   gas detection means for continuously detecting the presence of at least one gas in the observed zone, said gas detection means collecting radiant flux coming from the observed zone and analyzing absorbance in a plurality of different spectral bands of the radiant flux;
   a Fourier transform infrared spectroscope for performing a spectral analysis of the radiant flux, wherein the Fourier transform infrared spectroscope has a smaller angular aperture than the gas detection means; and
   a matrix of micromirrors, each micromirror individually steerable between at least two positions, wherein
      in a first position each micromirror reflects the radiant flux coming from the observed zone to the gas detection means for detecting the presence of at least one gas in the radiant flux, and
      in a second position each micromirror reflects the radiant flux coming from the observed zone to the Fourier transform infrared spectroscope for performing the spectral analysis of the radiant flux
   wherein the micromirrors of the matrix of micromirrors are controlled to steer one or more of the micromirrors from the first position to the second position such that the matrix of micromirrors simultaneously reflects radiant flux from the observed zone to both the gas detection means and the Fourier transform infrared spectroscope.

2. A detector device according to claim 1, wherein the gas detection means analyzes absorbance in at least six different spectral bands to detect gas in said at least six different spectral bands.

3. A device according to claim 1, wherein said matrix of micromirrors comprises a substrate on which each micromirror is hinged to pivot between the first and second positions by using means for applying an electrostatic field between the substrate and the micromirror.

4. A device according to claim 1, wherein each of the micromirrors is steerable about a pivot so as to cover an angular extent of about 24°.

5. A method of using a detector device for optically detecting a gas in an observed zone of space, the detector device comprising: gas detection means for continuously detecting the presence of at least one gas in the observed zone, said gas detection means collecting radiant flux coming from the observed zone and analyzing absorbance in a plurality of different spectral bands of the radiant flux; a Fourier transform infrared spectroscope for performing a spectral analysis of the radiant flux, wherein the Fourier transform infrared spectroscope has a smaller angular aperture than the gas detection means; and a matrix of micromirrors, each micromirror individually steerable between at least two positions, wherein (i) in a first position each micromirror reflects the radiant flux coming from the observed zone to the gas detection means for detecting the presence of at least one gas in the radiant flux, and (ii) in a second position each micromirror reflects the radiant flux coming from the observed zone to the Fourier transform infrared spectroscope for performing the spectral analysis of the radiant flux, the method comprising:
   a) causing the micromirrors of the matrix to be steered simultaneously so that all of the radiant flux coming from the observed zone is directed to the gas detection means;
   b) deducing the presence of a gas, if any, in a portion of the observed zone on the basis of an analysis of the plurality of different spectral bands;
   c) in the event of the presence of a gas being detected in a portion of the observed zone, steering one or more of the micromirrors corresponding to said portion of the observed zone into the second position, while maintaining one or more of the micromirrors in the first position so as to simultaneously reflect radiant flux from the observed zone to both the gas detection means and the Fourier transform infrared; spectroscope; and
   d) confirming or invalidating the presence of the detected gas on the basis of a Fourier transform analysis provided by the Fourier transformation infrared spectroscope.

6. A detector device according to claim 1, wherein said gas detection means is a spectral band camera.

7. A detector device according to claim 1, wherein said gas detection means includes one or more filters, each filter having a respective wavelength transmission band.

8. A detector device according to claim 1, wherein said gas detection means includes at least one sensitive element onto which an image is formed, said image reflected by said matrix of micromirrors.

9. A method according to claim 5, wherein said gas detection means is a spectral band camera.

10. A detector device according to claim 1, wherein said gas detection means includes an optical system.

11. A detector device according to claim 1, wherein the Fourier transform infrared spectroscope calculates a concentration of the detected gas.

12. A method according to claim 5, wherein said method further comprises:

e) determining a concentration of the detected gas on the basis of the spectral analysis of the radiant flux performed by the Fourier transform infrared spectroscope.

\* \* \* \* \*